US008891713B2

(12) United States Patent
Zhang (10) Patent No.: US 8,891,713 B2
(45) Date of Patent: Nov. 18, 2014

(54) SYSTEM FOR ADAPTIVE SAMPLED MEDICAL SIGNAL INTERPOLATIVE RECONSTRUCTION FOR USE IN PATIENT MONITORING (75) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 361 days.

(21) Appl. No.: 13/345,807

(22) Filed: Jan. 9, 2012

(65) Prior Publication Data
US 2012/0257698 A1 Oct. 11, 2012

Related U.S. Application Data (60) Provisional application No. 61/472,325, filed on Apr. 6, 2011.

(51) Int. Cl.
H04L 7/00 (2006.01)
H03M 1/12 (2006.01)
A61B 5/04 (2006.01)
A61B 5/0428 (2006.01)
A61B 5/0456 (2006.01)

(52) U.S. Cl.
CPC ......... H03M 1/1265 (2013.01); A61B 5/04017 (2013.01); A61B 5/0428 (2013.01); A61B 5/0456 (2013.01)
USPC ............................ 375/355; 375/224; 375/371

(58) Field of Classification Search
USPC .......................................................... 375/355
See application file for complete search history.

(56) References Cited

U.S. PATENT DOCUMENTS

| 4,048,443 | A | * | 9/1977 | Crochiere et al. | ............ 704/206 |
| 4,594,576 | A | | 6/1986 | Fujii | |
| 5,187,482 | A | | 2/1993 | Tiemann et al. | |
| 5,241,310 | A | | 8/1993 | Tiemann | |
| 5,433,208 | A | * | 7/1995 | Lundstrom et al. | ........... 600/508 |
| 5,477,472 | A | | 12/1995 | Wise et al. | |
| 5,691,720 | A | | 11/1997 | Wang et al. | |
| 5,963,160 | A | | 10/1999 | Wilson et al. | |
| 6,191,718 | B1 | | 2/2001 | Matsumoto | |
| 6,240,132 | B1 | | 5/2001 | Yedid | |
| 6,259,997 | B1 | * | 7/2001 | Sasho et al. | ..................... 702/60 |
| 6,266,581 | B1 | * | 7/2001 | Wheatley et al. | ............. 700/302 |
| 6,462,693 | B1 | | 10/2002 | Rivoir | |
| 6,498,823 | B1 | * | 12/2002 | Samueli et al. | ............... 375/371 |
| 6,584,162 | B1 | | 6/2003 | Tinker | |
| 6,642,863 | B1 | | 11/2003 | Venkitachalam et al. | |
| 6,686,860 | B2 | | 2/2004 | Gulati et al. | |
| 6,717,540 | B1 | | 4/2004 | Kamas | |
| 6,937,946 | B1 | * | 8/2005 | Culp et al. | ..................... 702/62 |
| 6,943,716 | B2 | | 9/2005 | Mallinson | |

(Continued)

Primary Examiner — Lihong Yu
(74) Attorney, Agent, or Firm — Brennan K Bradley (57) ABSTRACT A patient medical signal processing system adaptively reconstructs a medical signal sampled using a varying sampling rate. The system includes an input processor and a signal processor. The input processor receives first data and second data. The first data represents a first portion of a medical signal derived by sampling at a first sampling rate and the second data represents a second portion of the medical signal derived by sampling at a second sampling rate. The first and the second sampling rates are different and comprise a master clock rate or an integer division of the master clock rate. A signal processor provides a reconstructed sampled medical signal by, interpolating the second data to provide third data at the first sampling rate and combining the first data and the third data to provide the reconstructed sampled medical signal.

20 Claims, 9 Drawing Sheets

(56) References Cited

U.S. PATENT DOCUMENTS

| | | |
|---|---|---|
| 6,999,014 B2 | 2/2006 | Oliaei et al. |
| 7,148,834 B2 | 12/2006 | Dias |
| 7,248,200 B2 | 7/2007 | Komuro et al. |
| 7,295,645 B1 | 11/2007 | El-Ghoroury et al. |
| 7,330,138 B2 | 2/2008 | Mallinson et al. |
| 7,336,208 B2 | 2/2008 | Van Den Enden |
| 7,739,049 B2 * | 6/2010 | Market et al. ............ 702/6 |
| 7,876,251 B2 | 1/2011 | Zhang |
| 7,952,425 B2 | 5/2011 | Zhang et al. |
| 8,262,578 B1 * | 9/2012 | Bharmi et al. ............ 600/484 |
| 2003/0067404 A1 | 4/2003 | Ruha et al. |
| 2003/0078007 A1 | 4/2003 | Parssinen et al. |
| 2004/0218074 A1 * | 11/2004 | Fossum ............ 348/272 |
| 2010/0056897 A1 | 3/2010 | Zhang |
| 2010/0165204 A1 * | 7/2010 | Huang et al. ............ 348/581 |

* cited by examiner

SYSTEM FOR ADAPTIVE SAMPLED MEDICAL SIGNAL INTERPOLATIVE RECONSTRUCTION FOR USE IN PATIENT MONITORING

This is a non-provisional application of provisional application Ser. No. 61/472,325 filed Apr. 6, 2011, by H. Zhang.

FIELD OF THE INVENTION

This invention concerns a patient medical signal processing system for adaptively reconstructing a medical signal sampled using a varying sampling rate.

BACKGROUND OF THE INVENTION

High resolution signals in patient monitoring and recording systems are used to detect and characterize small changes and distortion in patient signals, such as electrocardiogram (ECG), intra-cardiac electrogram (ICEG) and blood pressure signals, especially nonlinear, non-stationary and non-uniform changes and jittering within patient signals. Known medical signal conversion and acquisition systems typically employ linear and uniform analogue to digital conversion of patient signals for high resolution signal acquisition with continuous high sampling rate. However this high data acquisition rate may lead to over-sampling of signals and generate excessive amounts of data, and pose an additional processing burden in signal filtering, data compression and transmission. Additionally, in many medical signals from a patient (e.g. surface ECG signals, intra-cardiac electrograms), the portion of interest of the signal, such as a QRS complex is of higher frequency than remaining portions of the signal and may comprise a small portion (e.g. 15-30%) of the whole signal cycle.

Known systems use linear and uniform sampling and data acquisition. The data conversion usually involves sampling at 2-5 times the maximum frequency of the medical signals (according to the Nyquist-Shannon sampling theorem) to achieve adequate signal quality. The known sampling systems may cause over-sampling and redundant data acquisition and may fail to adequately sample fast activity wave portions and may over sample in relatively low frequency wave portions. Further, known medical recording and analysis systems based on linear data sampling and acquisition, offer limited sampling control and sensitivity particularly in the presence of noise and may distort derived signal frequency spectrum data. A system according to invention principles addresses these deficiencies and related problems.

SUMMARY OF THE INVENTION

A system provides adaptive data sampling and an adaptive data acquisition rate based on signal intrinsic characteristics, to capture and characterize real time dynamic patient medical signals. A patient medical signal processing system adaptively reconstructs a medical signal sampled using a varying sampling rate. The system includes an input processor and a signal processor. The input processor receives first data and second data. The first data represents a first portion of a medical signal derived by sampling at a first sampling rate and the second data represents a second portion of the medical signal derived by sampling at a second sampling rate. The first and the second sampling rates are different and comprise a master clock rate or an integer division of the master clock rate. A signal processor provides a reconstructed sampled medical signal by, interpolating the second data to provide third data at the first sampling rate and combining the first data and the third data to provide the reconstructed sampled medical signal.

DETAILED DESCRIPTION OF THE INVENTION

Definitions

Uniform data sampling comprises sampling signals (analogue waveforms) with a uniform time interval between samples. Non-uniform and nonlinear sampling comprises sampling signals based on signal characteristics or changes and sampling with high rate during high signal activity and low sampling rate during low signal activity. The time interval between data sampling points is different and time interval distribution is typically not uniform.

A system uses nonlinear and non-uniform data sampling, conversion and acquisition with optimized and adaptive data sampling and adaptive acquisition rate based on signal content intrinsic characteristics, to capture and characterize real time dynamic patient medical signals. The system employs nonlinear, non-stationary and non-uniform data sampling and signal construction to provide high resolution signal monitoring, data filtering and waveform smoothing. The system further characterizes different kinds of small changes and distortions within real time acquired patient signals by automatically adaptively altering analogue to digital conversion parameter configuration and tuning. Furthermore, the system reduces digital data conversion time and resource burden.

The system interpolates nonlinearly and non-uniformly sampled digital signal data based on automatically determined signal content intrinsic characteristics and a user determined anatomical region of interest (ROI). Different sampling rates are adaptively used for sampling different portions of a signal nonlinearly and non-uniformly in response to determined signal characteristics. The system automatically adaptively varies sampling rate in response to ROI location in a heart cycle, signal morphology, dynamic frequency range, instantaneous frequency, and activity, signal type and data indicating a medical procedure or event. The inventor has advantageously recognized that signal processing is improved by adaptive use of different sampling rates for different types of portion of a patient signal. The inventor has also advantageously recognized that signal processing is improved by use of non-linear frequency band control in a noisy environment and by use of smart user pre-determined sampling methods based on patient event, signal significance, data identifying a medical procedure and a clinical application concerned, for example. The resulting system provides signal reconstruction using nonlinear and non-uniform signal interpolation.

For example, in an ECG signal (Electrophysiological signals), a dynamic signal portion (in particular the high frequency portion) is usually the QRS complex associated with depolarization comprising about 15-30% of a whole heart beat cycle, which is advantageously sampled at a higher sampling rate (such as 400-1000 Hz). The remaining portions of the heart beat signal involve relatively lower frequency signals which do not need such fast rate sampling and data conversion. Analog to digital conversion (A2D) control is important in medical signal sampling and data acquisition. Typically a high speed analogue to digital converter is utilized for a known high frequency content signal or unknown signals. The system advantageously adaptively tunes and controls an A2D module based on input signal content for use in early stage myocardial ischemia detection and comparison methods together with nonlinear and non-uniform signal and data sampling.

Figure 1:
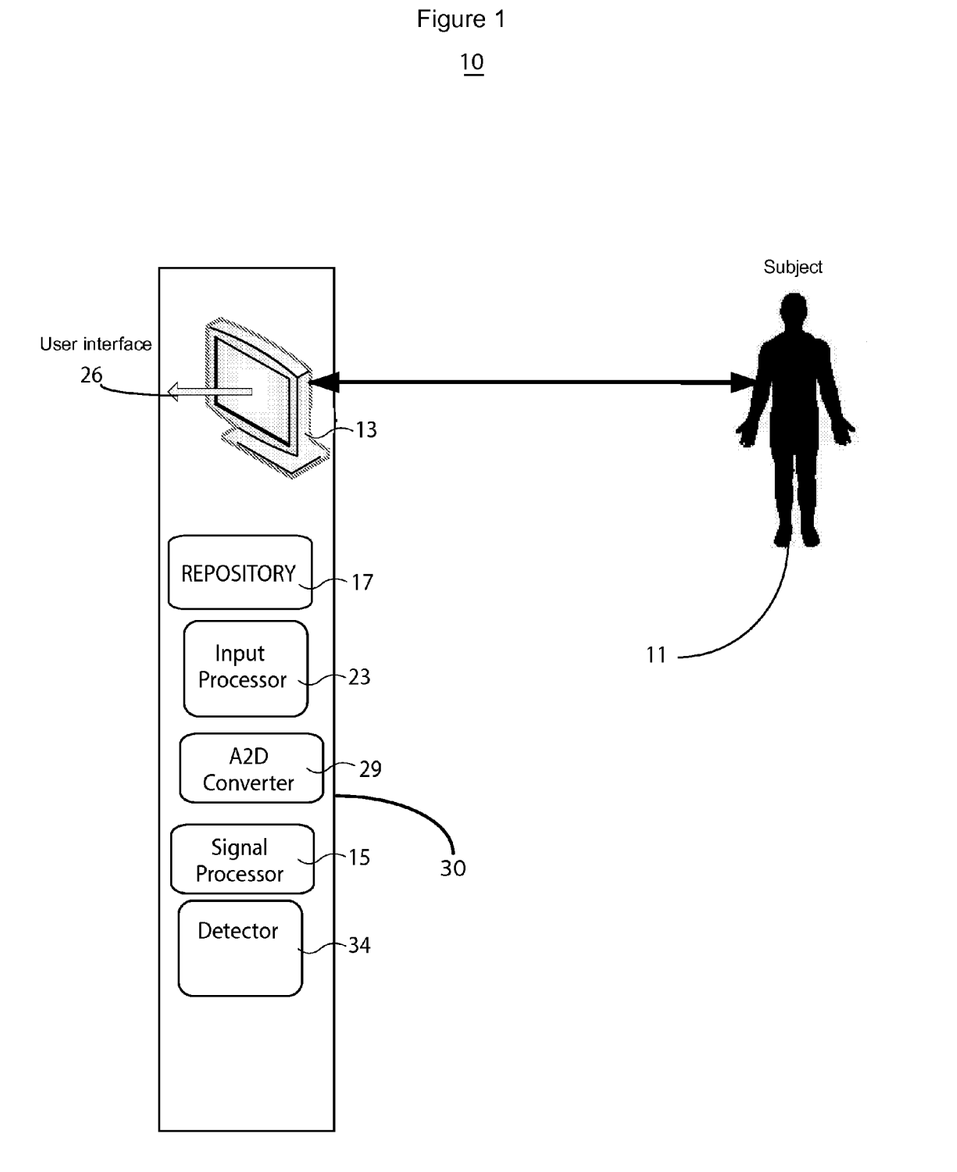
FIG. 1 shows a patient medical signal processing system for adaptively reconstructing a medical signal sampled using a varying sampling rate, according to invention principles.

FIG. 1 shows patient medical signal processing system 10 for adaptively reconstructing a medical signal sampled using a varying sampling rate. System 10 comprises at least one computer system, workstation, server or other processing device 30 including, reproduction device 13, repository 17, signal processor 15, input processor 23, detector 34, A2D (analog to digital) converter 29, and a user interface 26. Input processor 23 receives first data and second data. The first data represents a first portion of a medical signal derived by sampling at a first sampling rate. The second data represents a second portion of the medical signal derived by sampling at a second sampling rate. The first and the second sampling rates are different and comprise a master clock rate or an integer division of the master clock rate. Signal processor 15 provides a reconstructed sampled medical signal by, interpolating the second data to provide third data at the first sampling rate and combining the first data and the third data to provide the reconstructed sampled medical signal. Detector 34 detects the first and second portions within a cycle of the medical signal using a peak detector and by segmenting the signal into windows where the waves are expected and identifying the peaks within the windows. Analog to digital converter 29 adaptively digitizes an analog cyclically varying medical signal derived from a patient in response to a first sampling rate to provide the first data representing the first portion of the medical signal and in response to a second sampling rate clock to provide the second data representing the second portion of the medical signal.

Figure 2:
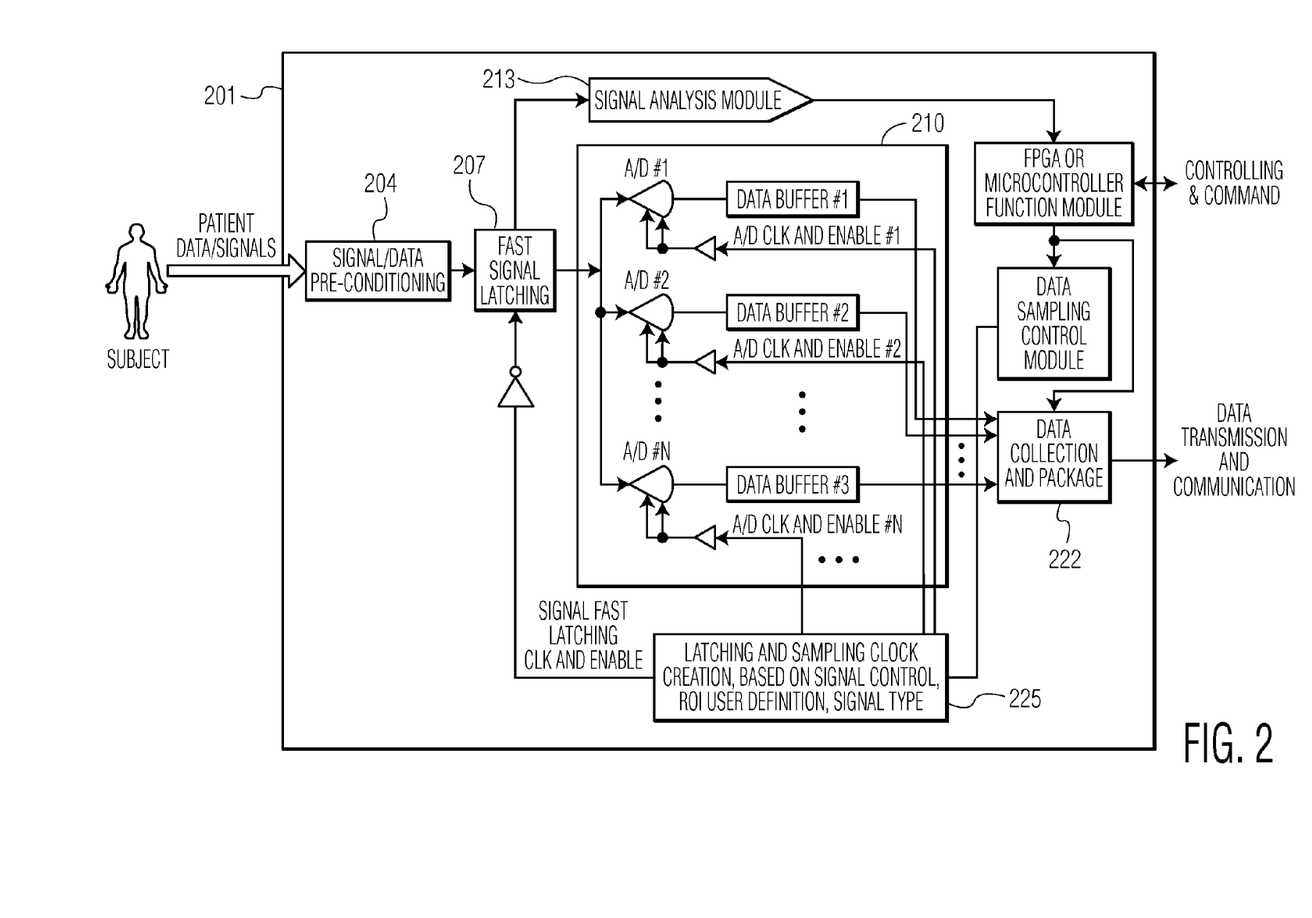
FIG. 2 shows a block diagram of a system for nonlinear and non-uniform based medical signal sampling and data acquisition using automatic A2D control, according to invention principles.

FIG. 2 shows a block diagram of system 201 for nonlinear and non-uniform based medical signal sampling and data acquisition using automatic A2D control. Acquired patient data includes electrophysiological signals (such as surface ECG signal, intra-cardiac electrograms), hemodynamic signals (such as pressure, blood parameter) and vital signs signals and images. Signal pre-conditioning (filtering and buffering) is performed in unit 204 and the resultant signal is latched by unit 207. This unit performs a fast latching function to generate a stable analogue signal for A/D conversion by A2D converter 210. The digitized signal data from converter 210 is collated, packaged and buffered for output by unit 222 as resultant multi-channel data (non-uniform data) for communication, in compressed or non-compressed form by wired or wireless communication.

Unit 213 analyzes and characterizes patient signals provided by latch 207 by deriving signal content information concerning patient signal frequency band including data identifying a highest instantaneous frequency component of the signal, detecting events and signal type (ECG/ICEG/SPO2/IBP) and by selecting particular signal portions for analysis. The signal content information derived by unit 213 is provided to controller 216 (e.g. an FPGA or microprocessor). Controller 216, in response to the signal content information, directs A2D conversion and output via control of units 219, 222 and 225. Specifically, controller 216 directs unit 219 in response to signal content information, in selecting a sample rate and adjusting an associated time clock to be used by A2D converter 210 for processing incoming medical signals. Controller 216 directs unit 225 in response to signal content information, in control of latching and selection of the number of A2Ds to be activated and method of cooperation of the selected number of A2Ds.

Figure 3:
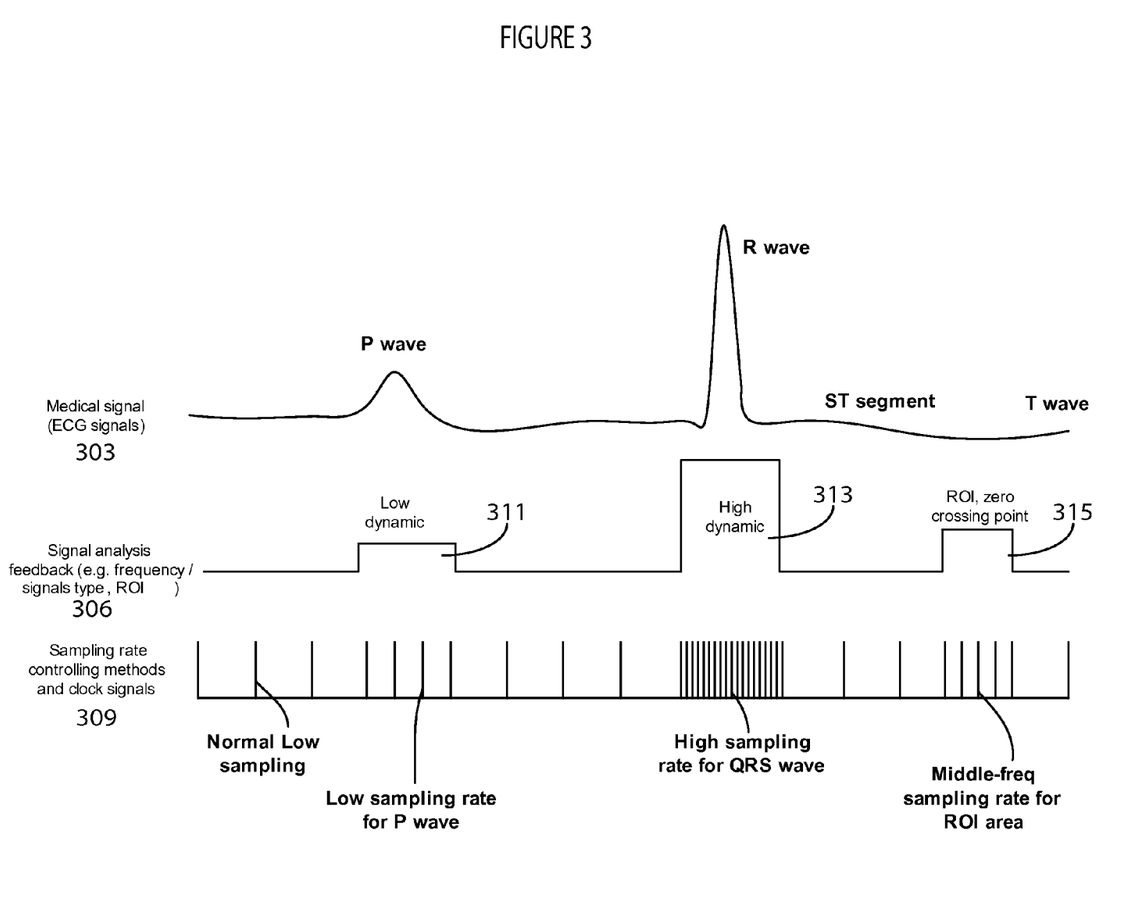
FIG. 3 shows system sample rate control for an episode of a surface ECG signal involving nonlinear and non-uniform data sampling, according to invention principles.

FIG. 3 shows system sample rate control for an episode of a surface ECG signal involving nonlinear and non-uniform data sampling. Single lead surface ECG signal 303 has a signal activity frequency range between 0 and 200 Hz. System 201 (FIG. 2) identifies and uses different sampling rate regions having different sampling rate. The surface ECG signal 303 waveform comprises a P wave, QRS complex, ST segment, T wave, and low activity/rest waves. The sampling rate and frequency are advantageously adaptively controlled in real time by system 201 using software and/or firmware in processing devices 216, 219, 222 and 225, for example. Different methods are used by system 201 to adaptively control signal sampling and digital data acquisition of different significant timing portions including signal, P wave, R wave and ST segment. In response to unit 213 determining a peak signal frequency in a P wave signal portion, the P wave is sampled and digitized by A2D converter 210 using a relatively low sampling rate while a QRS wave is sampled and digitized by A2D converter 210 using a relatively high frequency sampling rate.

Although the ST segment and T wave are low frequency signals, the ST segment zero crossing point (crossing a zero DC voltage level of signal 303) is an important clinical indicator. Therefore this region of interest (ROI) of signal 303 encompassing the zero crossing point is selected in response to predetermined stored information (or by a user via input command) to be sampled and digitized by A2D converter 210 using higher resolution sampling to improve signal quality and facilitate medical diagnosis. System 201 similarly identifies and selects a ROI for detection of a parameter associated with different predetermined thresholds, such as for a warning threshold voltage and a threshold associated with signal 303 slope (rate of change) or acceleration. Identified regions of adaptively selected sampling rate are shown by region selection signal 306 indicating P wave low sampling rate portion 311, QRS high sampling rate portion 313 and middle range sampling rate zero crossing portion 315. The associated sampling clock signal is shown in signal 309. Approximately 100 sample points are used in a whole heart cycle in total, for example, whereas a known linear data sampling system acquires 200 points for this same ECG episode with reduced data timing accuracy than the system nonlinear and non-uniform sampling method.

A quantized clock is used in order to achieve accurate and appropriate signal and waveform construction from a non-uniform sampled data series. In the example in FIG. 3, the highest sampling rate is assigned to a QRS wave portion which is 4096 samples per second (4K Hz); Middle frequency/resolution sampling rate is assigned to ST segment to T wave portion which is 1024 sample points per second (1K Hz) based on clinical application and requirements of ST segment timing; a P wave is sampled with low resolution data rate which is about 128 Hz. For the cardiac rest portion of a signal (non-ROI, non-event, non-activity signal portions), the sampling rate is 16 Hz. The signal portion determination and sampling rate are controlled adaptively by the system.

System 201 generates and uses a synchronized sampling rate sequence for non-uniform data sampling. In order to provide this sequence, system 201 generates a central high frequency, e.g. $f_{base}$ clock and derives sub-clocks in response to predetermined stored signal intrinsic activity characteristic indicators or user command, such as predetermined information in a lookup table associating multiple different signal frequency ranges with a corresponding maximum clock frequency. For example, in FIG. 3, a QRS wave sampling clock is automatically selected to be $$\frac{1}{2}f_{base}$$

while a sampling rate for the ST segment portion is selected as $$\frac{1}{8}f_{base}.$$

Therefore, sub-level non-uniform sampling rates are advantageously phase locked with base central frequency $f_{base}$ and phase and timing conditions for A2D conversion are stable. This decreases system sampling deviation and noise and provides high sampling rate, high resolution digitized signals.

Figure 4:
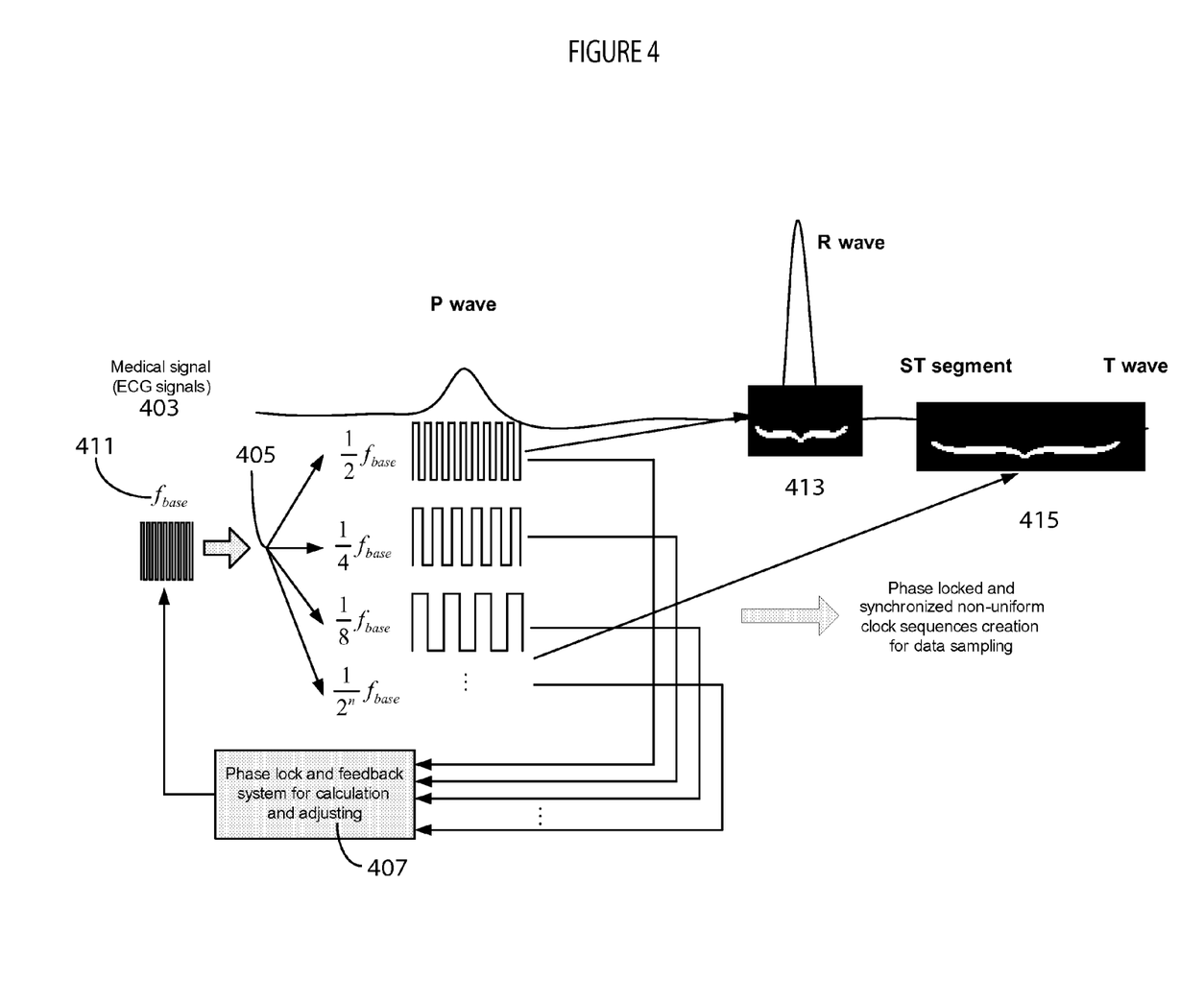
FIG. 4 illustrates non-uniform data sampling, latching and acquisition based on quantized data sampling rate, according to invention principles.

FIG. 4 illustrates non-uniform data sampling, latching and acquisition based on quantized data sampling rate and shows a method for generating synchronized non-uniform phase locked sample clocks. Sub-level clocks 405 are generated for sampling ECG signal 403 in a quantized manner comprising $$\frac{1}{2^n}f_{base}$$

of the based clock 411 and used for A2D conversion of QRS portion 413 and ST segment zero crossing portion 415, for example. Clock generation and adaptive clock selection, adjustment and control are provided by unit 407.

The system employs different kinds of sub-clock generation and phase locking. The generated sample clocks may comprise $$\frac{1}{3}f_{base}, \frac{1}{5}f_{base} \ldots \frac{1}{n}f_{base}.$$

However, generated non-quantized clock sequences may have relative phase deviation and result in differences in A2D conversion including locking and sampling phase differences. This may lead to jitter and distortion in resultant digitized signal construction and subsequent signal processing. In contrast, generated quantized sub clocks advantageously provide a high resolution and synchronized data acquisition.

Nonlinear and non-uniform signal sampling and data acquisition are used by system 201 for A2D signal conversion and to capture and record signal changes and functional clinical activity. However, resultant signal data acquisition information densities vary over time in real time data sampling. Hence, non-uniform signal interpolation and nonlinear filtering functions are advantageously utilized to derive final uniform high resolution patient signals, which are processed using a Fast Fourier Transform (FFT) frequency analysis, wavelet analysis and/or entropy analysis, for example. In one heart signal cycle, a QRS wave, T wave and P wave, are sampled and digitized with different sampling rates, $$\frac{1}{2}f_{base}, \frac{1}{4}f_{base},$$

for example. The system advantageously employs different kinds of signal interpolation adaptively selected in response to signal ROI specific content information provided by unit 213 (FIG. 2). Selected types of interpolation include, linear interpolation (AR modeling, sine modeling, for example) and nonlinear interpolation (probability estimation, Fuzzy modeling, artificial neural network estimation and statistical possibility estimation, for example). In one embodiment, high order AR (Autoregressive) modeling is used for QRS waveform interpolation while low order AR modeling may be used for P wave interpolation. A semi-AR model calculation of signal amplitude magnitude is used to estimate a middle point amplitude by nonlinear weight averaging (using an AR model to estimate characteristics of subsequent input data by using previously acquired data). The semi-AR modeling is also used for nonlinear averaging to calculate interesting signal point values by using several data points around a point of interest.

Different semi-AR modeling or nonlinear estimation functions are adaptively selected and used for data interpolation of corresponding different signal portions, such as for interpolation of a P wave portion and QRS wave portion in response to signal content information provided by unit 213. In one embodiment, a method for adaptive interpolation function selection for different signal portions involves the assumption that in one patient signal cycle, different portions are using different kinds of averaging semi-AR model and distribution and the assumption that each portion of the patient signal is one semi-AR model distribution. The data sample magnitude distribution is also based on the signal semi-AR estimation and calculation. Multiple different semi-AR models may be used for corresponding different portions of a heart electrical activity representative signal. The different models include, semi-AR model #1 for a QRS waveform, semi-AR model #2 for a P wave.

For a patient, coefficients in a semi-AR model are adaptively varied in response to detected cardiac arrhythmias and events. However in one stable cycle, semi-AR model coefficients are stable and constant. The following equation is for sample magnitude estimation using multi semi-AR models selected in response to signal portion information content.

$$mag(x) = \begin{cases} \text{Semi-AR\_model\#1}(x) = \sum_{i=1}^{P_1} \alpha_{1i} \cdot x_i; & \text{signal\_\#1} \\ \vdots & \\ \text{Semi-AR\_model\#}n(x) = \sum_{i=1}^{P_n} \alpha_{ni} \cdot x_i; & \text{signal\_\#}n \end{cases}$$

where, semi-AR_model # n stands for a model for signal portion #n, $P_n$ is the number of samples used in semi-AR_model # n for estimation of a signal magnitude value of an interpolation point, $\alpha_{ni}$ are coefficient weight values for an interpolation sample magnitude calculation. Nonlinear semi-AR models (in which each portion of a semi-AR model is linear) are used in a polynomial calculation with appropriate coefficients for signal interpolation of different signal portions. However different methods may be used for interpolation of signal magnitude, such as a fuzzy model or an ARMA model. The number of the data points (such as $x_i$) neighboring point of interest x, used for calculation of the amplitude of point x, may be adaptively varied in response to an accuracy determination or detected signal noise, for example, (low signal to noise ratio may require more data points $x_i$ for improved estimation of x). Hence the window size ($P_n$) for the semi-AR modeling interpolation is selected and determined adaptively by the system or by a user.

An interpolation calculation based on nonlinear semi-AR modeling includes performing nonlinear and non-uniform sampling and A2D data conversion. A semi-AR method is selected to perform first level data interpolation and double the non-uniform data. Additional iterative data interpolation may be performed to increase data points. The semi-AR modeling interpolation is repeated to derive signal information of desired detail.

Figure 5:
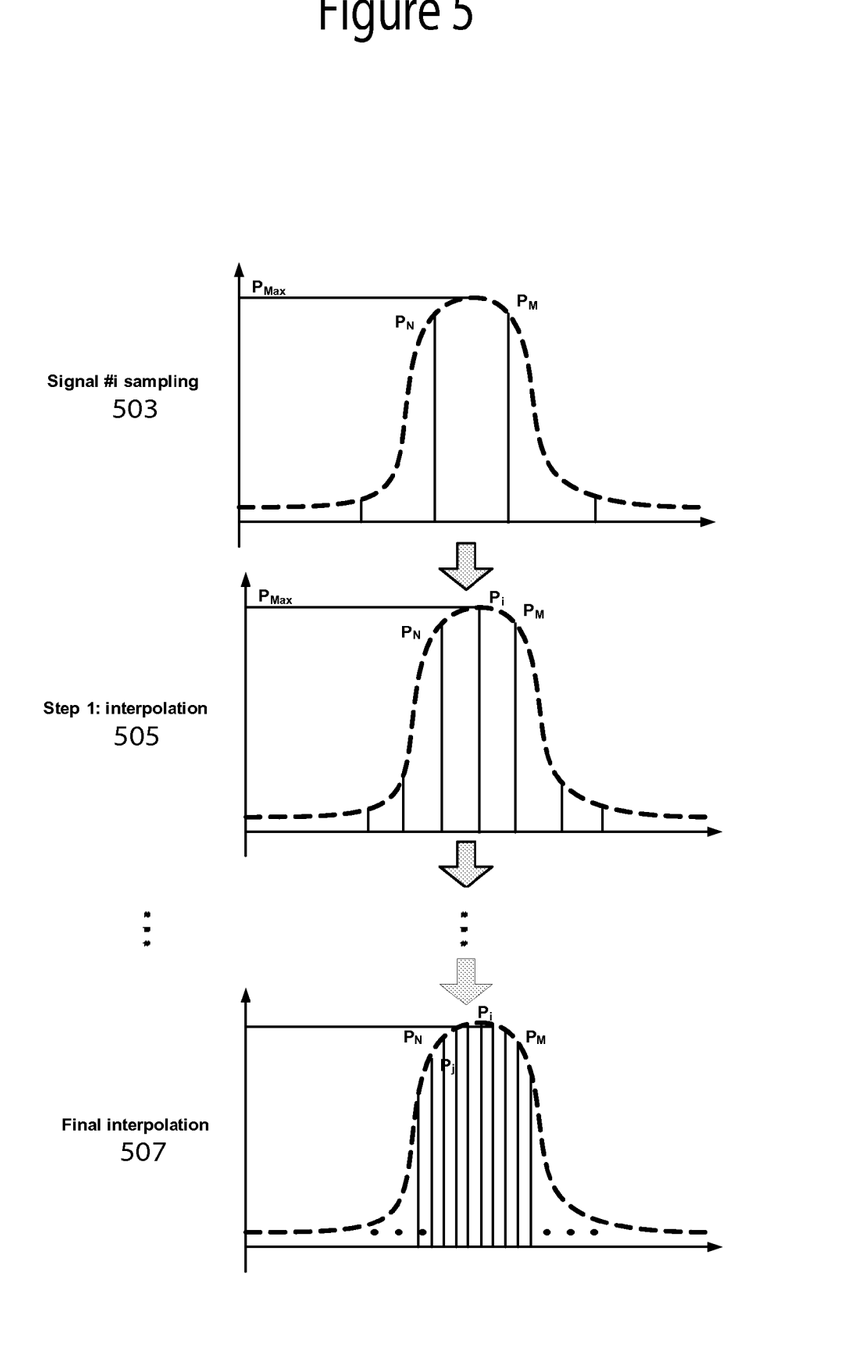
FIG. 5 illustrates an interpolation using semi-AR (semi-autoregressive) modeling and calculation to estimate neighbor sample point magnitudes and values, according to invention principles.

FIG. 5 illustrates an interpolation using semi-AR modeling to estimate neighbor sample point magnitudes and values. Multiple level interpolations are used to interpolate points of signal portion 503 to provide signal portion 505 and to interpolate points of signal portion 505 to provide signal portion 507. Usually a semi-AR model coefficient is fixed and stable, but the coefficient values may be time varying in response to patient status. Modeling and estimation facilitates estimation of higher resolution data for a patient signal. However due to function limitations, abrupt jumping and jittering in the data sample estimation and calculation may occur. Therefore nonlinear or non-uniform filtering using a controllable bandwidth filter as shown in FIG. 6 is used for cleaning and smoothing the interpolated signals and waveforms.

Figure 6:
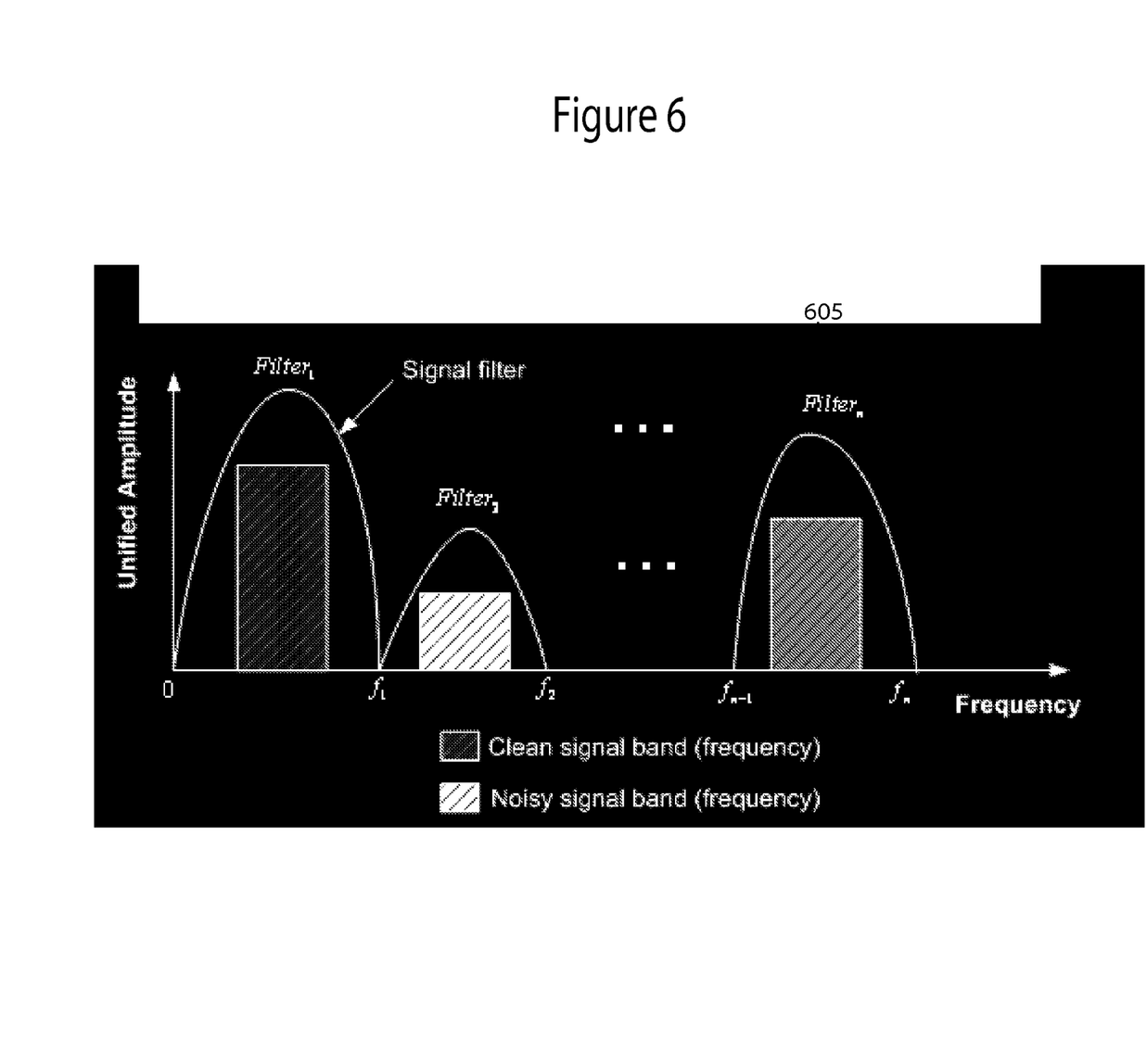
FIG. 6 shows a method of non-uniform and nonlinear frequency band control of filters for interpolating and smoothing a signal, according to invention principles.

FIG. 6 shows a method of non-uniform and nonlinear frequency band control of filters for interpolating and smoothing a signal. The frequency band control is performed in response to an adaptive tunable frequency band selector. Noise is mainly focused in the frequency band $f_1$-$f_2$ and hence the adaptive controller adjusts the parameters of Filter 2 603 to decrease the noise and enhance output signal quality and signal to noise ratio (SNR) in response to feedback. The adaptive controller further adjusts the parameters of Filter n 605 to provide specific filters to decrease corresponding specific noise and enhance output signal quality and signal to noise ratio (SNR) in response to feedback. The system uses non-uniform filtering and interpolation to improve a signal for analysis, such as cardiac arrhythmia detection and characterization. The system adaptively selects filter characteristics for different portions of a patient heart electrical activity representative signal and for different heart electrical activity signals of a heart conveyed on different catheter channels for example as well as for different types of signals.

In non-uniform filtering, adaptive multi-frequency band filters (including at least two different frequency band filters) and automatic close-loop (feedback) control are utilized to achieve real-time gain adjustment within individual frequency bands and to improve signal to noise ratio. In optimization of the signal to noise ratio $$\Phi(\text{signal}) = f(A_1 + A_2 + \ldots + A_n)$$

$\Phi(\bullet)$ is a function value of the signal noise ratio, $f(\bullet)$ is a function used to calculate and summarize the signal, $A_i$ is the gain of the $i^{th}$ frequency band. The filtering achieves optimum signal quality, if $\Phi(\text{signal})$ reaches the biggest value.

Figure 7:
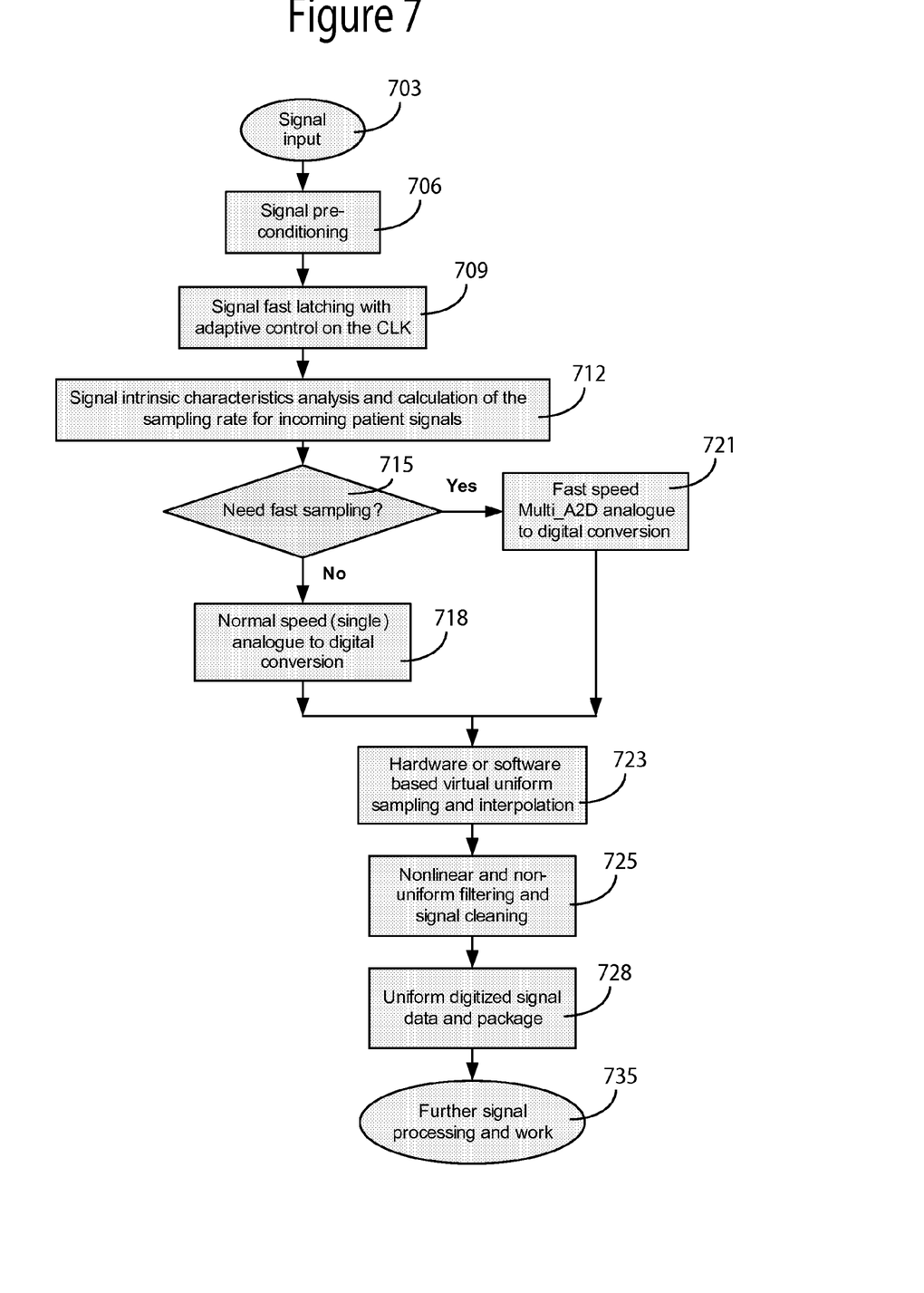
FIG. 7 shows a flowchart of a method for adaptive non-uniform signal and data sampling and acquisition, according to invention principles.

FIG. 7 shows a flowchart of a method for adaptive non-uniform signal and data sampling and acquisition performed by the system of FIG. 2. An input medical signal (such as ECG, ICEG) is analyzed for characteristics after signal pre-conditioning, such as buffering, filtering amplification. Based on the signal analysis the system adaptively selects sampling rate. In response to input medical signal content the system employs uniform or non-uniformed signal data acquisition. For non-uniform data sampling, virtual uniform sampling interpolation and nonlinear filtering are used to create a uniform data set which is further processed.

Unit 204 pre-conditions a signal in step 706 following acquisition of the signal in step 703 and the resultant signal is latched by unit 207 in step 709 in response to an adaptively controlled clock signal. In step 712, unit 213 analyzes and characterizes patient signals provided by latch 207 by deriving signal content information concerning individual patient signal frequency bands including data identifying a highest instantaneous frequency component of the signal and by detecting events and signal type (ECG/ICEG/SPO2/IBP) and by selecting particular signal portions for analysis. The system automatically selects non-uniform and nonlinear patient signal sampling and acquisition characteristics in response to signal content information based non-uniform and nonlinear sampling rate control. In one embodiment, predetermined knowledge of patient physiological signal characteristics such as information indicating an ECG signal is periodic having a particular cycle length range is used for signal portion detection (such as for RR wave detection) and to determine a ROI in a real time input signal.

A signal processor in controller 216 detects peaks of P Q R waves within the received sampled data by synchronization of a heart electrical activity waveform and peak detection of an R wave using a known peak detector and by identifying peaks of other waves by segmenting the signal represented by the sampled data into windows where the waves are expected and identifying the peaks within the windows. The Start point of a P wave, for example, is identified by a variety of known different methods. In one method the P wave start point comprises where the signal crosses a baseline of the signal (in a predetermined P wave window, for example). The baseline of the signal may comprise a zero voltage line if a static (DC) voltage signal component is filtered out from the signal.

Controller 216 in step 715, in response to the signal content information, selects an A2D sampling rate for individual portions of the latched signal in a heart cycle and directs A2D conversion and output using a selected sampling rate via control of units 219, 222 and 225. In response to determination that a heart cycle signal portion has relatively high peak frequency content, unit 216 selects a number of A2D units and directs A2D 210 conversion using a relatively high sampling rate in step 721. In response to determination that another different heart cycle signal portion has relatively low peak frequency content, unit 216 selects a number of A2D units and directs A2D 210 conversion using a relatively low sampling rate in step 718. Unit 222 in step 723 under direction of controller 216 uses non-uniform and nonlinear interpolation by adaptively interpolating individual sampled data representing the individual signal portions using respective selected corresponding interpolation functions. Non-uniform and nonlinear interpolation is used to provide sampling data at the highest rate of the signal sampling. Processing of a slow medical signal is sampled at an appropriate slow sampling rate in response to determination by a recognition and adjustment module in unit 216 to capture needed detail. Sampling rate and construction level (the resolution needed) is controlled by controller 216.

In step 725 unit 222 adaptively filters individual interpolated sampled data representing the individual signal portions using respective selected corresponding filter functions. In step 728 unit 222 combines the filtered individual interpolated sampled data representing different heart cycle signal portions to provide a reconstructed sampled medical signal. In step 735 unit 222 provides additional filtering and packaging to provide the reconstructed sampled medical signal. The system acquires a high resolution patient signal during high frequency signal activity, such as a QRS portion of an ECG signal to facilitate identification of distortion of signal morphology and a zero crossing of an ST segment. The system performs zero crossing point detection and characterization and detection of a zero crossing point in a PQ portion and ST wave. The delay of a zero crossing point may indicate pathology or an event in the cardiac issue and electrophysiological response signals.

Figure 8:
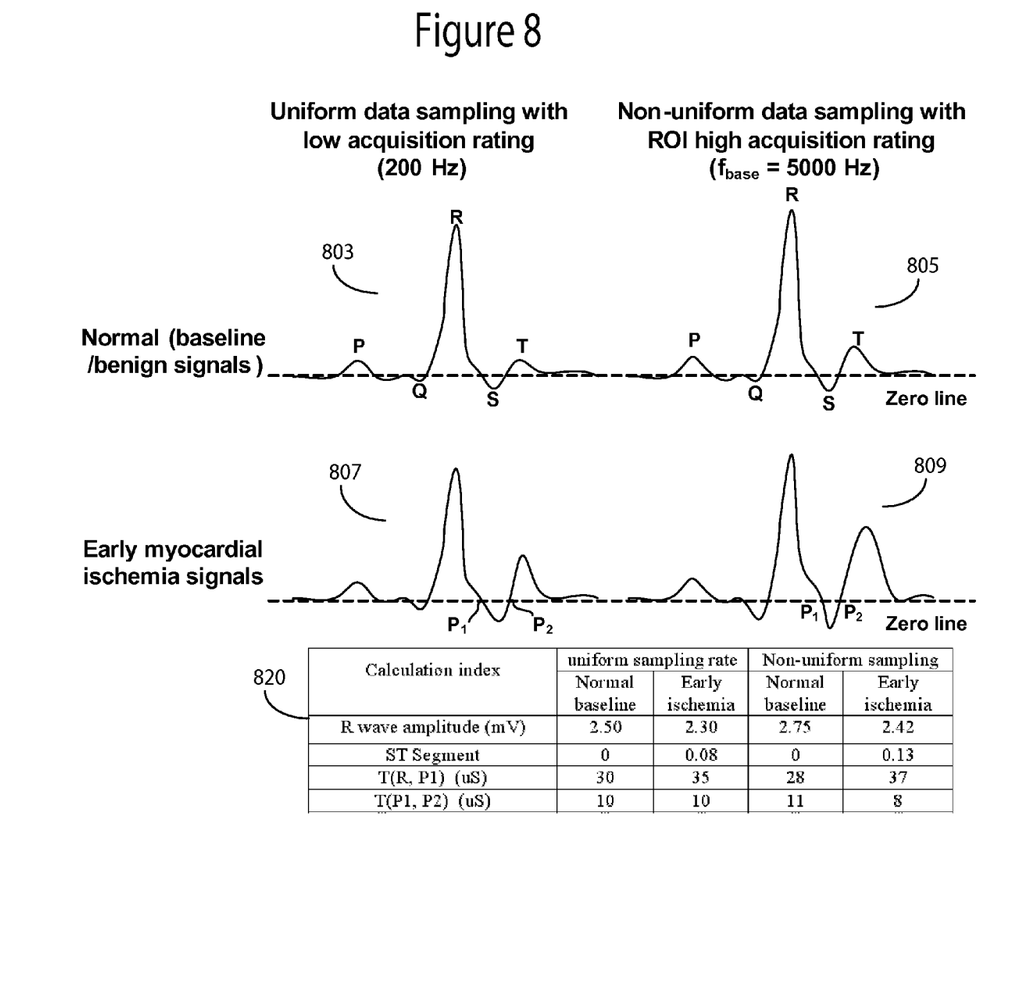
FIG. 8 shows a simulation of myocardial ischemia detection and diagnosis, according to invention principles.

FIG. 8 shows a simulation of myocardial ischemia detection and diagnosis comprising myocardial ischemia signal sample comparison, event detection, and signal morphology comparison. Normal episodes (waveforms 803, 805) and abnormal episodes (waveforms 807, 809) of a Lead II surface ECG signal with normal uniform sampling (803, 807) and non-uniform (805, 809) sampling are shown and compared. Non-uniform ECG signal sampling is used to detect an R wave peak value increase and to detect R wave amplitude and ST segment changes (used for clinical myocardial ischemia identification). Measurements are compared in Table 820 for the normal and abnormal signals processed using known signal processing and system 10 non-uniform sampling with relative high sampling rate in a ROI. Table 820 comparison measurements include R wave peak amplitude, T(R, P1) and T(P1, P2). Where, T(R, P1) comprises a time interval between an R wave and P1 (e.g. 813, a zero crossing point before a successive S wave). Also T(P1, P2) comprises a time interval between P1 (e.g. 813) and P2 (e.g. 815), zero crossing points associated with an S wave.

As shown by table 820, for normal (healthy or benign) signals, a known uniform signal sampling method indicates R wave amplitude is 2.5 mV while a non-uniform sampling method employed by system 10 (FIG. 1) indicates R wave amplitude is 2.75 mV. During the early myocardial ischemia events, the R wave amplitudes for known uniform and system 10 non-uniform sampling are 2.30 mV and 2.42 mV, respectively. Known uniform 200 Hz sampling rate has a 5 mS (millisecond) resolution which is of negligible use for timing analysis. In contrast, system 10 adaptively adjusts non-uniform sampling to improve resolution by controlling sampling rate of an ECG (or other) signal in a ROI. The system 10 determined T(R, P1) and T(P1, P2) time intervals of table 820 show 9 ms and 3 ms differences, respectively between normal and abnormal signals which are substantially greater than the known sampling rate derived corresponding time interval values. The system advantageously identifies the substantial difference using nonlinear and non-uniform sampling. The system may be implemented in an integrated controllable and programmable A2D device and is used for analyzing other types of signal such as temperature, energy and pressure signals. Pre-knowledge of a medical signal being analyzed is advantageously used in nonlinear and non-uniformed sampling and data acquisition for configuring adaptability.

Figure 9:
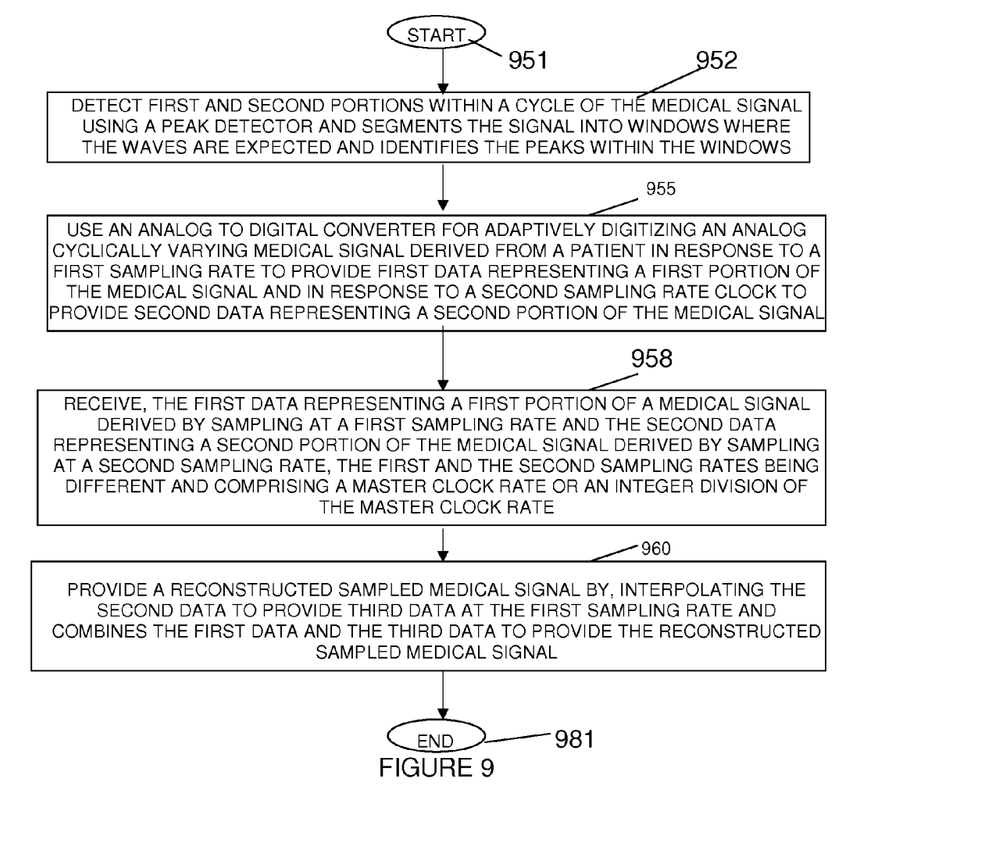
FIG. 9 shows a flowchart of a process used by a patient medical signal processing system for adaptively reconstructing a medical signal sampled using a varying sampling rate, according to invention principles.

FIG. 9 shows a flowchart of a process used by patient medical signal processing system 10 (FIG. 1) for adaptively reconstructing a medical signal sampled using a varying sampling rate. Detector 34 in step 952 following the start at step 951 detects first and second portions within a cycle of the medical signal using a peak detector and segments the signal into windows where the waves are expected and identifies the peaks within the windows. In step 955 analog to digital converter 29 adaptively digitizes an analog cyclically varying medical signal derived from a patient in response to a first sampling rate to provide first data representing a first portion of the medical signal and in response to a second sampling rate clock to provide second data representing a second portion of the medical signal.

In step 958, input processor 23 receives, the first data representing the first portion of a medical signal derived by sampling at a first sampling rate and the second data representing the second portion of the medical signal derived by sampling at a second sampling rate. The first and the second sampling rates are different and comprise a master clock rate or an integer division of the master clock rate. Specifically, in one embodiment, the first and the second sampling rates comprise a division of the master clock rate by 2 to the power n where n is an integer. In step 960, signal processor 15 provides a reconstructed sampled medical signal by, interpolating the second data to provide third data at the first sampling rate and combines the first data and the third data to provide the reconstructed sampled medical signal. Further, signal processor 15 interpolates the first data to provide fourth data at the first sampling rate and combines the fourth data and the third data to provide the reconstructed sampled medical signal. In one embodiment processor 15 adaptively varies sampling rate in response to a dynamic changing characteristic of the medical signal including rate of change of said medical signal and/or to comprise a non-uniform and nonlinear sampling rate.

Signal processor 15 linearly interpolates the second data to provide the third data using at least one of, (a) data within the second portion, (b) data in a signal portion adjacent the second portion and (c) data of a substantially whole heart cycle. In one embodiment, signal processor 15 interpolates the second data using a weighted averaging interpolation. Alternatively, signal processor 15 nonlinearly interpolates the second data to provide the third data using at least one of, (a) a semi-autoregressive model, (b) an autoregressive moving average model and a fuzzy model. In another embodiment, signal processor 15 nonlinearly interpolates the second data using at least one of, (a) data within the second portion, (b) data in a signal portion adjacent the second portion and (c) data of a substantially whole heart cycle. The process of FIG. 9 terminates at step 981.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The processes and applications may, in alternative embodiments, be located on one or more (e.g., distributed) processing devices on a network linking the system units. Any of the functions and steps provided in the Figures may be implemented in hardware, software or a combination of both.

The system and processes of FIGS. 1-9 are not exclusive. Other systems and processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system adaptively uses different sampling rates and number of analog to digital converters in sampling and digitizing different types of portion of a patient signal and adaptively interpolates the digitized data in response to frequency and other characteristics of the content of the patient signal. Further, the processes and applications may, in alternative embodiments, be located on one or more (e.g., distributed) processing devices on a network linking the units of FIG. 1. Any of the functions and steps provided in FIGS. 1-9 may be implemented in hardware, software or a combination of both.

What is claimed is:

1. A patient medical signal processing system for adaptively reconstructing a cardiac signal sampled using a varying sampling rate, comprising:
   an input processor for receiving,
      first data representing a first portion of a cardiac signal derived by sampling at a first sampling rate and
      second data representing a second portion of said cardiac signal derived by sampling at a second sampling rate, said first and said second sampling rates being different and comprising a master clock rate or an integer division of said master clock rate; and
   a signal processor for providing a reconstructed sampled cardiac signal by,
      interpolating said second data to provide third data at said first sampling rate,
      providing at least two different specific filters for respective different frequency bands of said third data,
      adaptively adjusting, in response to feedback, one or more parameters of at least one of the different specific filters to decrease corresponding specific noise, and
      combining said first data and said third data to provide said reconstructed sampled cardiac signal.

2. The system according to claim 1, wherein said signal processor interpolates said first data to provide fourth data at said first sampling rate and combines said fourth data and said third data to provide said reconstructed sampled cardiac signal.

3. The system according to claim 1, wherein said one or more parameters comprise a gain of the at least one of the different specific filters.

4. The system according to claim 1, wherein said signal processor linearly interpolates said second data to provide said third data.

5. The system according to claim 4, wherein said signal processor linearly interpolates said second data using at least one of, (a) data within said second portion, (b) data in a signal portion adjacent said second portion and (c) data of a substantially whole heart cycle.

6. The system according to claim 1, wherein said signal processor interpolates said second data using a weighted averaging interpolation.

7. The system according to claim 1, wherein said signal processor nonlinearly interpolates said second data to provide said third data.

8. The system according to claim 1, wherein said signal processor nonlinearly interpolates said second data using at least one of, (a) a semi-autoregressive model, (b) an autoregressive moving average model and a fuzzy model.

9. The system according to claim 7, wherein said signal processor nonlinearly interpolates said second data using at least one of, (a) data within said second portion, (b) data in a signal portion adjacent said second portion and (c) data of a substantially whole heart cycle.

10. The system according to claim 1, including
   an analog to digital converter for adaptively digitizing an analog cyclically varying cardiac signal derived from a patient in response to the first sampling rate to provide said first data representing said first portion of said cardiac signal and in response to the second sampling rate to provide said second data representing said second portion of said cardiac signal.

11. The system according to claim 1, including
a detector for detecting the first and second portions within a cycle of said cardiac signal using a peak detector and segmenting the signal into windows where waves are expected and identifying peaks within the windows.

12. A patient medical signal processing system for adaptively reconstructing a medical signal sampled using a varying sampling rate, comprising:
an input processor for receiving,
first data representing a first portion of a medical signal derived by sampling at a first sampling rate and
second data representing a second portion of said medical signal derived by sampling at a second sampling rate, said first and said second sampling rates being different and comprising a master clock rate or a division of said master clock rate by 2 to a power n where n is an integer; and
a signal processor for providing a reconstructed sampled medical signal by,
interpolating said second data to provide third data at said first sampling rate,
providing at least two different specific filters for respective different frequency bands of said third data,
adaptively adjusting, in response to feedback, one or more parameters of at least one of the different specific filters to decrease corresponding specific noise, and
combining said third data and said first data to provide said reconstructed sampled medical signal.

13. A method for processing a patient medical signal to adaptively reconstruct a cardiac signal sampled using a varying sampling rate, comprising the steps of:
receiving first data representing a first portion of a cardiac signal derived by sampling at a first sampling rate;
receiving second data representing a second portion of said cardiac signal derived by sampling at a second sampling rate, said first and said second sampling rates being different and comprising a master clock rate or a division of said master clock rate by 2 to a power n where n is an integer;
adaptively selecting, in response to signal content information associated with said second portion, an autoregressive or semi-autoregressive interpolation function for interpolating said second data;
interpolating, using selected interpolation function, said second data to provide third data at said first sampling rate; and
combining said third data and said first data to provide said reconstructed sampled cardiac signal.

14. The method according to claim 13, including the step of adaptively varying said first sampling rate in response to a dynamic changing characteristic of said cardiac signal including rate of change of said cardiac signal.

15. The method according to claim 13, including the step of adaptively varying said first sampling rate to comprise a non-uniform and nonlinear sampling rate in response to a dynamic changing characteristic of said cardiac signal including rate of change of said cardiac signal.

16. The method according to claim 13, including the step of providing at least two different specific filters for respective different frequency bands of said third data; and
adaptively adjusting, in response to feedback, one or more parameters of at least one of the different specific filters to decrease corresponding specific noise.

17. The method according to claim 16, wherein the one or more parameters comprise a gain of the at least one of the different specific filters.

18. The method according to claim 16, wherein the one or more parameters comprise a frequency band of the at least one of the different specific filters.

19. The method according to claim 13, wherein adaptively selecting the autoregressive or semi-autoregressive interpolation function comprises adaptively varying coefficients in a semi-autoregressive model.

20. The method according to claim 13, wherein adaptively selecting the autoregressive or semi-autoregressive interpolation function comprises selecting a high order autoregressive model for a QRS segment of the cardiac signal and selecting a low order autoregressive model for a P wave segment of the cardiac signal.

* * * * *